(12) United States Patent
Xiang et al.

(10) Patent No.: US 8,664,238 B2
(45) Date of Patent: Mar. 4, 2014

(54) INDENOISOQUINOLINONE DERIVATIVES, MANUFACTURING METHOD AND MEDICAL USE THEREOF

(75) Inventors: Hua Xiang, Jiangsu (CN); Tianlin Wang, Jiangsu (CN); Hong Xiao, Jiangsu (CN); Qidong You, Jiangsu (CN); Yao Yao, Jiangsu (CN); Xiaobo Li, Jiangsu (CN); Qingjiang Liao, Jiangsu (CN)

(73) Assignees: China Pharmaceutical University, Nanjing, Jiangsu (CN); Nanjing Medical University Affiliated Brain Hospital, Nanjing, Jiangsu (CN)

( * ) Notice: Subject to any disclaimer, the term of this patent is extended or adjusted under 35 U.S.C. 154(b) by 0 days.

(21) Appl. No.: 13/643,314

(22) PCT Filed: Dec. 16, 2009

(86) PCT No.: PCT/CN2009/075618
§ 371 (c)(1),
(2), (4) Date: Dec. 14, 2012

(87) PCT Pub. No.: WO2011/047515
PCT Pub. Date: Apr. 28, 2011

(65) Prior Publication Data
US 2013/0085140 A1    Apr. 4, 2013

(30) Foreign Application Priority Data

Oct. 22, 2009 (CN) .......................... 2009 1 0233991

(51) Int. Cl.
*A61K 31/473* (2006.01)
*C07D 221/18* (2006.01)

(52) U.S. Cl.
USPC ........... 514/284; 546/61; 544/125; 514/232.8

(58) Field of Classification Search
USPC .................. 514/284, 232.8; 546/61; 544/125
See application file for complete search history.

(56) References Cited

PUBLICATIONS

Kim, S.H. et al.: Indeno[1,2-c] isoquinolines as enhancing agents on all-trans retinoic acid-mediated differentiation of human myeloid leukemia cells. Bioorg. & Medicin. Chem., vol. 16, pp. 1125-1132, 2008.*

* cited by examiner

*Primary Examiner* — Charanjit Aulakh
(74) *Attorney, Agent, or Firm* — Global IP Services; Tianhua Gu

(57) ABSTRACT

Indenoisoquinolinone derivatives (I), the manufacturing method and the medical use thereof, which belong to pharmaceutical chemistry and organic chemistry field, are disclosed. These compounds can be used for treating several medical symptoms related to postmenopausal syndrome, uterine fibers deterioration and aortic smooth muscle cells proliferation, especially ER-(+) depend breast cancer. Meanwhile, these compounds can also be used for treating glioma and lung cancer, and have inhibiting effect on tumor metastasis effect on tumor metastasis.

5 Claims, No Drawings

INDENOISOQUINOLINONE DERIVATIVES, MANUFACTURING METHOD AND MEDICAL USE THEREOF

CROSS REFERENCE TO RELATED PATENT APPLICATION

The present application is the US national stage of PCT/CN2009/075618 filed on Dec. 16, 2009, which claims the priority of the Chinese patent application No. 200910233991.7 filed on Oct. 22, 2009, which application is incorporated herein by reference.

FIELD OF INVENTION

The invention relates to the field of pharmaceutical chemistry and organic chemistry, especially relates to indenoisoquinolinone derivatives. These compounds can be used for the treatment of several medical indications related to the postmenopausal syndrome, the deterioration of uterine fibers and the proliferation of aortic smooth muscle cells, especially ER dependent breast cancer. Meanwhile, these compounds can also be used for the treatment of glioma and lung cancer, and have inhibition effect on tumor metastasis.

BACKGROUND OF INVENTION

"Postmenopausal syndrome" refers to various pathologic conditions caused by the decline in estrogen secretion when women are in or have completed physiological metamorphosis, namely, menopause. It is mainly represented in osteoporosis, estrogen-dependent cancers (breast cancer, endometrial cancer and ovarian cancer), cardiovascular diseases and senile dementia, etc.

Osteoporosis is a systemic bone disease characterized in the low bone mass and the degeneration of bone tissue microstructure. The population suffering from the osteoporosis in China currently accounts for about 7% of the total population, in which, the number of female patients with osteoporosis is 4 times of that of male patients, most common in postmenopausal women. The osteoporosis is not only harmful to individuals, but also causes a large number of economic losses due to its long disease course and its sequelae resulting in that patients need long-term treatment and nursing care and more so in older patients. In addition, although it is generally believed that osteoporosis is not life-threatening, 20% to 30% mortality rate in elderly women is related to hip fractures and this mortality rate is, in large part, related to the postmenopausal osteoporosis. The treatment method which is widely accepted for postmenopausal osteoporosis today is estrogen replacement treatment, which, although can relieve symptoms, will also produce some significant side effects, mainly in that the estrogen simulates endometrial hyperplasia, sometimes resulting n the cyclical bleeding, and even the occurrence of endometrial cancer and breast cancer. Raloxifene is the first selective estrogen receptor modulator that is approved to be used in the treatment of osteoporosis, but it has the tendency to increase hot flash and uterine hemorrhage.

Uterine fiber deterioration (uterine fibroids) is an ancient but still existing clinical problem up to now, including uterine fibroids, metrauxe, hysteromyoma, myometrial hypertrophy, uterine fiber deterioration and fiber uterine tumors. Generally speaking, uterine fiber deterioration is a pathologic condition in that the fibrous tissue improperly deposits on the uterine wall. This is one of the reasons for dysmenorrhea and infertility in women. The exact cause of uterine fiber deterioration is still poorly understood, but there are evidences indicating that it is caused by an unsuitable response of fibrous tissue to hormone. The surgery is the most conventional method to treat uterine fiber deterioration, which is expensive and sometimes induces complications such as abdominal adhesion and infection. For some patients, the initial surgery is only a temporary treatment and the fibers will regrow. In these cases, the hysterectomy can effectively terminate the growth of fibers, but patients also lose fertility. This disease can also be treated by administrating antagonists of gonadotropin-releasing hormone, but the use of them is restricted to the risk of causing osteoporosis. Thus, a new method is required for the treatment of uterine fiber deterioration.

Breast cancer is another common disease in elderly women and its main chemotherapy is to use selective estrogen receptor modulators, of which tamoxifen is in the highest flight. However, tamoxifen has significant drawbacks in that it shows the nature of estrogen agonist in the uterus and has a stimulating effect on the uterine cancer cells.

Brain tumor diseases refer to intracranial tumors, which can be divided, according to the lesion sources, into primary brain tumors and metastatic tumors metastasized from lung tumors. Glioma is the most common intracranial malignancy, accounting for more than 50% of the primary tumors of the nervous system. It is a type of malignancies with great hazard, high morbidity and high mortality rate. At present, surgery is the preferred treatment of glioma. However, the glioma mostly shows infiltrative growth and it is difficult to do total resection in surgery, so the glioma will generally recrudesce soon after surgery. Chemotherapy is an important supplement to the treatment of glioma and the main drug is nitrosourea, alone, or in combination with other drugs. However, the effect of chemotherapy on glioma is not satisfied enough for at least two reasons. One is that the existence of blood brain barrier prevents anticancer drugs to enter into the brain and the other is that quite a part of tumors are resistant to anticancer drugs. It has been found in studies that the overexpressed protein kinase C (PKC) in human glioma is related to the occurrence and development of tumors. As an estrogen receptor modulator, tamoxifen is mainly used to treat breast cancer in clinic. However, it is also a broad spectrum PKC inhibitor which prevents the growth of cancer cells by inhibiting PKC activity. Therefore, it is considered as a broad-spectrum antineoplastic drug.

Lung cancer is also one of the most common malignancies, the mortality rate of which is the first in the world. From the perspective of clinical features, it is inclined to divide, internationally, the lung cancer into the small cell lung cancer and the non-small cell lung cancer. The non-small cell lung cancer accounts for more than 85% of lung cancers. With the development and application of chemotherapeutics and molecular targeted drugs as well as the development of multidisciplinary treatment model of lung cancer in recent years, the overall 5-year survival rate of lung cancer has been significantly improved. Platinum-based combined chemotherapy remains the standard first-line chemotherapy of the advanced non-small cell lung cancer. The application of pemetrexed and docetaxel in clinic has improved the survival rate, remission rate and life quality of patients suffering from lung cancers to some extent. American Society of Clinical Oncology (ASCO) pointed out, in Annual Progress Report (2008), that the first-line treatment of the non-small cell lung cancer by cetuximab in combination with chemotherapy can improve 21% survival rate of patents suffering from the advanced lung cancer. At present, the tumor biotherapy with the representative of molecular target therapeutic agents has brought a new hope to the treatment of lung cancer, and in the future, the research on the treatment of lung cancer should focus on the biomolecular targeted therapy in combination with the chemotherapy or the multi-targeted therapy in combination with the chemotherapy.

Tumor metastasis is a successional multi-step active process. Tumor cells reach another position or multiple positions along certain channels from the primary tumor through the lymphatic channel, blood and cavity, forming a new metastasis. There are mainly four approaches of tumor metastasis: local spreading—constantly infiltrating the surrounding tissue, known as direct spreading of malignancy; lymphatic infiltration—metastasis from a local lymphatic to the whole lymphatic; hematogenous metastasis—metastasis to tissues and organs rich in blood flow along with the blood flow; cavity planting—implantation metastasis of tumor cells to the chest, the abdomen and the spinal cord cavity. The lymphatic infiltration and hematogenous metastasis are more common in these four ways. The recurrence rate of 1 year after the tumor surgery in China is up to 60% currently and more than 80% patients die of tumor recurrence and metastasis. It can be seen that the inhibition of metastasis and recurrence is as important as the treatment of the tumor.

SUMMARY OF INVENTION

The invention discloses indenoisoquinolinone derivatives of formula I. Pharmacological experiments have shown that the compounds of the invention can be used for the alleviation of symptoms related to postmenopausal syndrome, especially ER-(+) breast cancer, cardiovascular pathologic conditions and osteoporosis. Meanwhile, compounds of the invention can also be used for the treatment of glioma and lung cancers and for the inhibition of tumor metastasis.

The invention provides a compound of formula I:

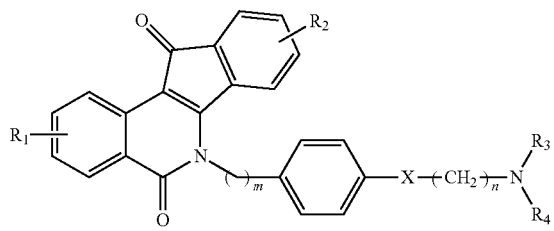

Wherein $R_1$ and $R_2$ independently represent H, OH, $C_1$-$C_4$ alkoxy or $C_1$-$C_6$ alkoxycarbonyl;

$R_3$ and $R_4$ independently represent —CO(CH$_2$)$_2$CH$_3$, —CO(CH$_2$)$_3$CH$_3$ or $C_1$-$C_6$ alkyl; or $R_3$ and $R_4$, when combined with their adjacent nitrogen atom, represent piperidyl, 2-methylpiperidyl, homopiperidyl, morpholinyl, pyrrolidinyl, 3-methylpyrrolidinyl, 3,3-dimethylpyrrolidinyl, 3,4-dimethoxypyrrolidinyl, piperazinyl, N-methylpiperazinyl, N-ethylpiperazinyl, N-phenylpiperazinyl or N-benzylpiperazinyl;

X represents O, S, NH, CH$_2$ or —CO—;

m=0 or 1; and n=2 or 3;

$R_1$ and $R_2$ preferably represent OH or methoxyl;

$R_3$ and $R_4$ preferably represent, when linked with N atom(s), pyrrolidinyl, piperidyl, methylpiperazinyl, methyl, ethyl, propyl, isopropyl, n-butyl, dimethylamino, diethylamino, dipropylamino, diisopropylamino or di-n-butylamino;

X preferably represents O or S, more preferably represents O.

The compound of formula I can be prepared by the following method:

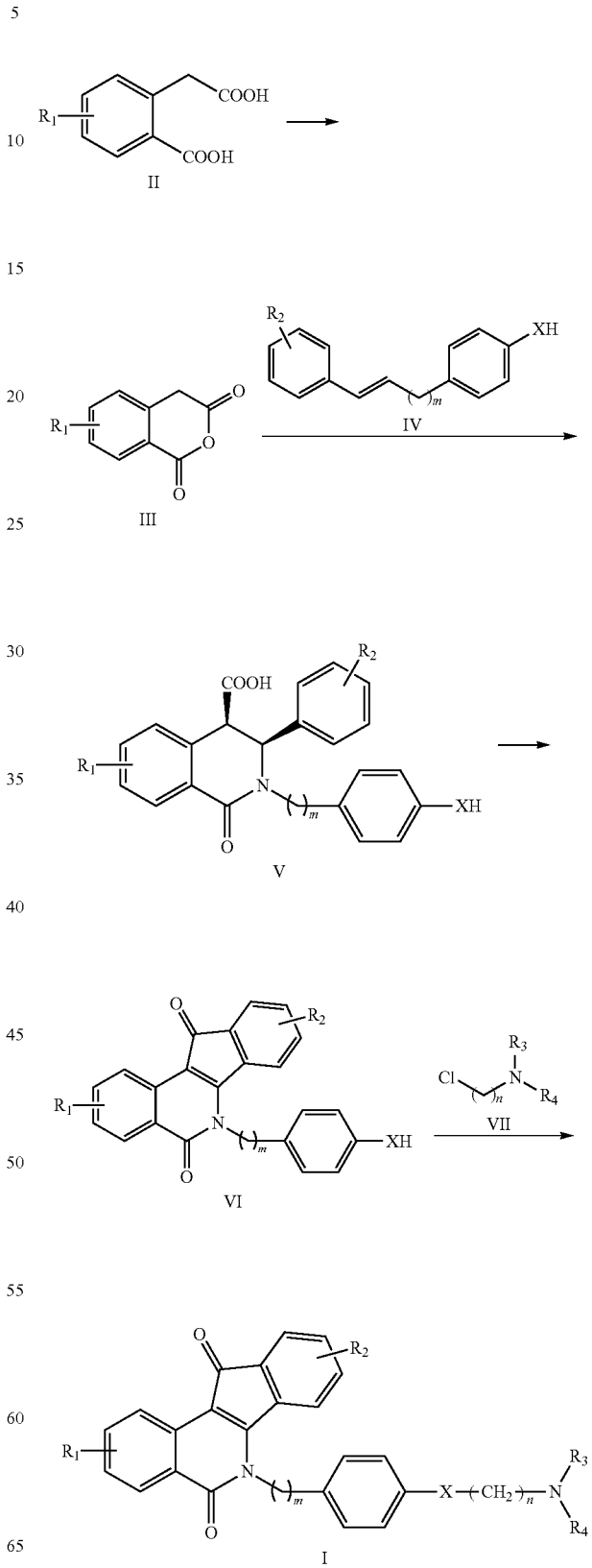

Wherein, $R_1$, $R_2$, $R_3$, $R_4$, X, n and m are defined as the above.

The structures of some compounds of the invention are as follows:

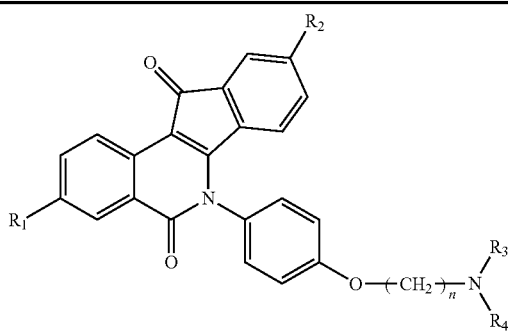

| Compound code | $R_1$ | $R_2$ | n | $R_3$, $R_4$ |
|---|---|---|---|---|
| I a | H | H | 2 | $(CH_2)_5$ |
| I b | H | H | 3 | $(CH_2)_5$ |
| I c | H | H | 2 | $CH_3$ |
| I d | H | H | 3 | $CH_3$ |
| I e | H | H | 2 | $CH_2CH_3$ |
| I f | H | H | 3 | $CH_2CH_3$ |
| I g | H | H | 2 | $((CH_2)_2)_2NCH_3$ |
| I h | H | H | 3 | $((CH_2)_2)_2NCH_3$ |
| I i | H | H | 2 | $(CH_2)_4$ |
| I j | H | H | 3 | $(CH_2)_4$ |
| I k | H | H | 2 | $CH(CH_3)_2$ |
| I l | H | H | 3 | $(CH_2)_2O(CH_2)_2$ |
| I m | H | H | 2 | $(CH_2)_2O(CH_2)_2$ |
| I n | $CH_3O$ | H | 2 | $CH_3$ |
| I o | OH | H | 2 | $CH_3$ |
| I p | $CH_3O$ | $CH_3O$ | 2 | $CH_3$ |
| I q | OH | OH | 2 | $CH_3$ |

Pharmaceutically acceptable salts formed from the compounds of the invention and acids are also included in the invention, and pharmaceutically acceptable salts can be form by the reaction of compounds of formula I with acids such as hydrochloric acid, sulfuric acid and maleic acid, etc.

The present invention further relates to a pharmaceutical composition containing the compound of formula I and pharmaceutically acceptable carriers. The composition optionally contains estrogen or progesterone. Herein the term "estrogen" includes steroids with estrogenic activities, such as 17-estradiol, estrone, conjugated estrogen, estrogen of female equine, 17-ethinyl estradiol, etc.; while the term "progesterone" includes compounds with progestational activities, such as lutocyclin, norethynodrel, megestrol acetate, norethindrone, etc.

The compounds of the invention can be formulated, alone or with one or more pharmaceutically acceptable carriers, to form preparations for administration. The compounds can be administrated in the form of oral formulas, such as tablets, capsules, dispersible powders and granules, etc., and can also be prepared as injectable preparations. These pharmaceutical preparations can contain an active ingredient of from 0.05% to 90% by weight, more commonly, from 15% to 60% by weight, and pharmaceutically acceptable carriers. The dose of the compound of the invention can be from 0.001 mg/kg/day to 100 mg/kg/day and can also deviate from this dose range according to different disease conditions or different dosage forms.

It is shown in pharmacological experiments that the compound of the invention can be used for alleviating the symptoms related to postmenopausal syndrome, especially ER-(+) breast cancer, cardiovascular pathologic conditions and osteoporosis. Meanwhile, these compounds can also be used for the treatment of glioma and lung cancers and the inhibition of tumor metastasis. The postmenopausal syndrome mainly includes osteoporosis, hysteromyoma, estrogen-dependent breast cancer, aortic smooth muscle cells proliferation or restenosis.

The followings are some pharmacological experiments and results of some compounds of the invention:

1. Experiment on the Proliferation of MCF-7 Breast Cancer Cells

The method described in Journal of Medicinal Chemistry. 1997. 40. 1407-1416 has been used and slightly modified.

1.1 Experimental Materials
1.1.1 Cell Line

Human breast cancer cells MCF-7, purchased from Nanjing Keygen Biotechnology Inc.

1.1.2 Reagents

RPMI1640 medium, anti-penicillin and anti-streptomycin double antibody, calf serum, purchased from GIBCO Company;

3-(4,5)-2-thiazolyl-(2,5)-dimethyl blue tetrazolium bromide (MTT), purchased from Sunshine Biotechnology (Nanjing) Co., Ltd;

All of the other reagents are analytically pure, produced domestically.

1.1.3 Main Experimental Instruments

American Revco $CO_2$ incubator; Labsystems Multiskan Ascent full-automatic ELIASA; German Carl Ziess Axiovert 40 CFL inverted fluorescence microscope 1.2 Experimental Methods
1.2.1 Cell Culture MCF-7 cells were incubated in RPMI1640 medium (containing 10% calf serum, 100 U/ml of penicillin and 100 μg/ml of streptomycin) in a 37° C. incubator with 5% $CO_2$. The medium was replaced once about two days and cells were subcultured once every 3-4 days. In the subculturing, the old medium was discarded and the culture was washed twice with D-hanks (for washing off the phenol red in the medium to eliminate the influence of phenol red on the digestion effect of trypsin). Then, a small amount of 0.25% trypsin (25 mg trypsin, 100 ml D-hanks) was added and the contents were paved in the bottle bottom smoothly. After digesting at 37° C. for about 2 min, cell rounding was observed with an inverted microscope. Trypsin was discarded and the cells were washed with D-hanks, then fresh medium was added and mixed by blowing. The cultures were put into new culture flasks and cultured continuously. After cell count, a small volume of cell suspension was taken and mixed with 0.4% trypan blue in the same volume by blowing with a straw. A little mixture (15 μl-20 μl) was taken and dropped into the interspace between the counting plate and the coverslip without bubbles. The mixture was observed with a 200× low magnification microscope. Dead cells can be stained by trypan blue, while living cells cannot. The counting plate was moved so as to see the counting squares, then unstained cells in four diagonal grids were counted. The cells counted include those on the right line and the top line but not those on the bottom line and the left line. The number of cells/ml=the number of cells in 25% grid×$10^4$.

1.2.2 MTT Detection Method

MCF-7 cells (1×$10^5$/ml) were inoculated into a 96-well plate and incubated for 24 h, then 100 μl drug-containing medium was added per well in the final concentrations of 1×$10^{-4}$ mol/L, 1×$10^{-5}$ mol/L, 1×$10^{-6}$ mol/L and 1×$10^{-7}$ mol/L, respectively, in tetra-plicate. The control group was that in which the anticancer drug was replaced with the same volume of medium and the blank group is 200 μl medium. After incubating for 48 h, 5 mg/ml MTT was added in 20 μl per well and the cultures were further incubated for 4 h. Then, the liquid was suck out carefully and 150 μl of DMSO was added per well. OD values of all wells were measured in 570 nm and the inhibition rate on the cell proliferation and values of $IC_{50}$ were calculated.

TABLE 1

Inhibition of compounds of the invention on the proliferation of MCF-7 breast cancer cells

| Compound code | $IC_{50}$ (μM) |
|---|---|
| Tamoxifen | 18.9 |
| Ia | 9.55 |
| Ib | 10.9 |
| Ic | 2.13 |
| Id | 27.9 |
| Ie | 7.8 |
| If | 8.52 |
| Ig | 5.82 |
| Ih | 5.89 |
| Ii | 11.3 |
| Ij | 24.7 |
| Ik | 79.9 |

The structures corresponding to the compound codes in Table 1 are the same as those in the former table.

Experiments on MCF-7 cells have been conducted for some synthetic indenoisoquinolinones with tamoxifen as a positive control. Results show that most of the compounds have good inhibitory activity in MCF-7 cells, and the activity of Compound Ic is the best with an $IC_{50}$ of 2.13 μM. Meanwhile, it can be observed that the compounds with a side chain containing 2 carbon atoms are generally better than those with a side chain containing 3 carbon atoms. It is inferred that a too long side chain affects the link of N atoms in the side chain with the corresponding amino acid residue, Asp351, of the estrogen receptor, and the 2-carbon-atom length just makes the side chain to be linked with Asp351. In addition, the compounds with a side chain substituted by methylpiperazine have shown a better activity no matter whether its side chain contains 2 carbon atoms or 3 carbon atoms, and it is inferred that the molecule containing two N atoms is well linked with the residue of Asp351.

Meanwhile, the proliferation experiment of H460 human lung cancer cells was also conducted. It is shown in the results that most of the compounds have inhibition effects on H460 cells, and the activity of compound If is the best with an $IC_{50}$ of 0.63 μM.

The scratch experiment of human umbilical vein endothelial cells (HUVEC) is conducted in vitro. It is shown in the results that most compounds can inhibit cell migration, suggesting that the compounds of the invention have a certain inhibiting effect on tumor metastasis.

DETAILED DESCRIPTION OF PREFERRED EMBODIMENTS

Example 1

Preparation of Homophthalic Anhydride (IIIa)

2 g (11.1 mmol) of homophthalic acid was dissolved in 30 ml toluene, and 1.6 ml (16.7 mmol) of acetic anhydride was added. The mixture was heated to the reflux temperature and reacted for 0.5 h. Then, the reaction mixture was cooled to the room temperature and concentrated to dry in a reduced pressure to obtain 1.8 g of a product as a pale yellow solid with the yield of 100%. m.p. 140-142° C.

Example 2

Preparation of 4-methoxyl homophthalic anhydride (IIIb)

1.1 g (5.2 mmol) of 4-methoxylhomophthalic acid (IIb) was dissolved in 20 ml toluene, and 0.7 ml (7.9 mmol) of acetic anhydride was added. The mixture was heated to the reflux temperature and reacted for 0.5 h. Then, the reaction mixture was cooled to the room temperature and concentrated to dry in a reduced pressure to obtain 1.1 g of a pale yellow solid with the yield of 100%. m.p. 142-143° C.

Example 3

Preparation of 4-benzylidene aminophenol (IVa)

2.1 g (19.3 mmol) of 4-aminophenol was dissolved in 28 ml ethanol, and 1.9 ml (19.3 mmol) benzaldehyde was added. The mixture was heated to the reflux temperature and reacted for 1.5 h, Then, the reaction mixture was cooled to the room temperature and the solid separated out from the mixture was filtered by sucking. The filter cake was washed with a small amount of ethanol and dried to obtain 3 g of a yellow solid with the yield of 76.9%. m.p. 182-183° C.

Example 4

Preparation of 4-(4-benzylidene amino) phenol (IVb)

0.9 g (8.23 mmol) of 4-aminophenol was dissolved in 15 ml ethanol, and 1 ml (8.8 mmol) of p-anisaldehyde was added. The mixture was heated to the reflux temperature and reacted for 4 h. Then, the reaction was cooled to room temperature, and the solid separated out from the mixture was filtered by sucking. The filter cake was washed with a small amount of ethanol and dried to obtain 1.37 g of a yellow solid with the yield of 73%. m.p. 188-189° C.

Example 5

Preparation of cis-N-(4-hydroxyphenyl)-1-oxo-3-phenyl-1,2,3,4-tetrahydroisoquinoline-4-carboxylic acid (Va)

0.65 g (4 mmol) of Compound IIIa was dissolved in 40 ml acetonitrile, and 0.79 g (4 mmol) of Compound IVa and 0.95 g (2 mmol) of $KAl(SO_4)_2 \cdot 12H_2O$ were added. The mixture was stirred at room temperature for 8 h, then filtered by sucking. The filter cake was washed with a small amount of acetonitrile, and dried to obtain 1.3 g of a pale yellow solid with the yield of 90.3%. m.p. 192-193° C. $^1$H-NMR (DMSO-$d_6$):9.48 (1H, s, OH), 6.64-8.07 (13H, m, Ar—H), 5.36 (1H, d, J=5.7 Hz, 3-H), 4.95 (1H, d, J=5.7 Hz, 4-H). EI-MS m/z: 359[M]$^+$.

Example 6

Preparation of cis-N-(4-hydroxyphenyl)-7-methoxyl-1-oxo-3-phenyl-1,2,3,4-tetrahydroisoquinoline-4-carboxylic acid (Vb)

0.98 g (5.1 mmol) of Compound IIIb was dissolved in 21 ml acetonitrile, and 1.1 g (5.6 mmol) of Compound IVa and 1.2 g (2.55 mmol) of $KAl(SO_4)_2·12H_2O$ were added. The mixture was sterred for 12 h at room temperature, then filtered by sucking. The filter cake was washed with a small amount of acetonitrile and dried to obtain 1.9 g of a pale yellow solid with the yield of 96%. m.p. 195-197° C. $^1$H-NMR (DMSO-$d_6$):9.45 (1H, s, OH), 6.64-7.56 (12H, m, Ar—H), 5.32 (1H, d, J=5.7 Hz, 3-H), 4.87 (1H, d, J=5.7 Hz, 4-H), 3.83 (3H, s, $CH_3O$). EI-MS m/z: 389[M]$^+$.

Example 7

Preparation of cis-N-(4-hydroxyphenyl)-7-methoxyl-3-(4-methoxyphenyl)-1-oxo-1,2,3,4-tetrahydroisoquinoline-4-carboxylic acid (Vc)

0.08 g (0.42 mmol) of Compound IIIb was dissolved in 21 ml acetonitrile, and 0.1 g (0.44 mmol) of Compound IVb and 0.1 g (0.21 mmol) $KAl(SO_4)_2·12H_2O$ were added. The mixture was sterred for 12 h at room temperature, then filtered by sucking. The the filter cake was washed with a small amount of acetonitrile, and dried to obtain 0.12 g of a pale yellow solid with the yield of 72%. m.p. 192-194° C. $^1$H-NMR (DMSO-$d_6$):9.47 (1H, s, OH), 6.64-7.52 (11H, m, Ar—H), 5.25 (1H, d, J=5.7 Hz, 3-H), 4.82 (1H, d, J=5.7 Hz, 4-H), 3.89 (3H, s, $CH_3O$), 3.83 (3H, s, $CH_3O$). EI-MS m/z: 419[M]$^+$.

Example 8

Preparation of 6-(4-hydroxyphenyl)-5H-indeno[1,2-c]isoquinoline-5,11(6H)-diketone (VIa)

1 g (2.8 mmol) of Compound Va was dissolved in 40 ml anhydrous toluene, and 4 ml (55.7 mmol) of thionyl chloride was added dropwise. The mixture was heated to the reflux temperature and reacted for 1.5 h, then the mixture was cooled to room temperature and concentrated to dry in a reduce pressure. 30 ml nitrobenzene was added to dissolve the residue, and 0.74 g (5.57 mmol) aluminum trichloride was added. The mixture was heated up to 100° C. and reacted for 0.5 h. Then, the reaction mixture was cooled to room temperature and poured into water. Into the lower organic layer obtained, cyclohexane was added, and the mixture was stirred until the solid is precipitated. The solid was filtered by sucking to obtain 0.55 g of a red solid with the yield of 58%. m.p. 274-280° C. $^1$H-NMR (DMSO-$d_6$):10.07 (1H, s, OH), 5.58-8.60 (12H, m, Ar—H). EI-MS m/z: 339[M]$^+$.

Example 9

Preparation of 6-(4-hydroxyphenyl)-3-methoxyl-5H-indeno[1,2-c]isoquinoline-5,11(6H)-diketone (VIb)

5.71 g (14.68 mmol) of Compound Vb was dissolved in 210 ml anhydrous toluene, and 21.3 ml (294 mmol) of thionyl chloride was added dropwise. The mixture was heated to the reflux temperature and reacted for 1.5 h. Then, the reaction mixture was cooled to room temperature, and concentrated to dry in a reduce pressure. 15 ml nitrobenzene was added to dissolve the residue, and 3.92 g (29.36 mmol) of aluminum trichloride was added. The mixture was heated up to 100° C. and reacted for 0.5 h, then cooled to room temperature and poured into water. Into the lower organic layer obtained, cyclohexane was added and the mixture was stirred until the solid is precipitated. The solid was filtered by sucking to obtain 4.17 g of a red solid with the yield of 77%. m.p. is over 300° C. $^1$H-NMR (DMSO-$d_6$): 10.05 (1H, s, OH), 5.52-8.54 (11H, m, Ar—H), 3.89 (3H, s, $CH_3O$). EI-MS m/z: 369[M]$^+$.

Example 10

Preparation of 6-(4-hydroxyphenyl)-3,9-dimethoxy-5H-indeno[1,2-c]isoquinoline-5,11(6H)-diketone (VIc)

0.3 g (0.72 mmol) of Compound Vc was dissolved in 10 ml anhydrous toluene, and 1 ml (14.3 mmol) of thionyl chloride was added dropwise. The mixture was heated to the reflux temperature and reacted for 1.5 h. Then, the mixture was cooled to room temperature and concentrated to dry in a reduced pressure. 15 ml Nitrobenzene was added to dissolve the residue, and 0.19 g (1.43 mmol) of aluminum trichloride was added. The mixture was heated up to 100° C. and reacted for 0.5 h, then cooled to room temperature and poured into water. Into the lower organic layer obtained, cyclohexane was added, and the mixture was stirred until the solid is precipitated. The precipitate was filtered by sucking to obtain 0.21 g of a red solid with the yield of 73%. m.p. is over 300° C. $^1$H-NMR ($CDCl_3$): 10.05 (1H, s, OH), 5.53-8.59 (10H, m, Ar—H), 3.87 (3H, s, $CH_3O$) 3.82 (3H, s, $CH_3O$). EI-MS m/z: 399[M]$^+$.

Example 11

Preparation of N-(2-chloroethyl) piperidine hydrochloride (VIIa)

170 g (2 mol) of piperidine, 67 ml (1 mol) of 2-chlorohydrin and 200 ml of toluene were added successively into a reaction flask. The mixture was heated to the reflux temperature and reacted for 3 h, then cooled to room temperature. The solid separated out was filtered by sucking and the filter cake was washed with 20 ml toluene. The temperature of the filtrate was controlled at about 75° C., then 200 ml of thionyl chloride was added dropwise. The mixture was refluxed for 2 h, then cooled to room temperature. The reaction mixture was concentrated to dry in a reduce pressure, and the residue was recrystallized with absolute ethyl alcohol to obtain 217 g of a white solid with the yield of 59.2%. m.p. 229-233° C.

Example 12

Preparation of N-(3-chloropropyl) piperidine hydrochloride (VIIb)

1.72 g (20.3 mmol) of piperidine, 2 ml (24.3 mmol) of 3-chloropropanol and 10 ml toluene were added successively into a reaction flask. The mixture was heated to the reflux temperature and reacted for 4 h. Into the reaction mixture, 5% NaOH 4 ml was added, and the mixture was refluxed for 1 h. After cooling to room temperature, the mixture was washed with 5% NaOH solution. The organic layer was washed with a saturated saline solution, then dried over anhydrous sodium sulfate and filtrated. 3 ml (40.6 mmol) thionyl chloride was added dropwise into the filtrate in an ice-bath, and the mixture was stirred at room temperature overnight. The reaction solution was concentrated to dry in a reduced pressure, and the residue was recrystallized with absolute ethyl alcohol to obtain 2.4 g of a khaki solid with the yield of 59%. m.p. 218-220° C.

Example 13

Preparation of 2-dimethylaminoethyl chloride hydrochloride (VIIc)

16.1 ml (0.24 mol) of 2-chlorohydrin was added dropwise into 13.4 ml (0.2 mol) of dimethylamine, and the mixture was heated to the reflux temperature and reacted for 4 h. After cooling to room temperature, 40 ml of 4N NaOH solution and 30 ml of benzene were added into the reaction mixture. The mixture was stirred vigorously, and a benzene layer was separated out after standing. The aqueous layer was washed with benzene, and the combined benzene layers were dried over anhydrous sodium sulfate and filtrated in a reduced pressure. The filtrate was concentrated to obtain 22 ml product, as an oil, and 40 ml of carbon tetrachloride was added to dissolve this oil. The solution was cooled by ice-water bath, and 10 ml solution of thionyl chloride dissolved in 10 ml carbon tetrachloride was added dropwise into the solution. The mixture was reacted for 4 h at room temperature, then concentrated to dry in a reduced pressure. The residue was recrystallized with ethyl acetate, and the crystal so obtained was dried to obtain 17.5 g of a white acicular crystal with the yield of 60.8%. m.p. 199-203° C.

Example 14

Preparation of 3-dimethylamino chloropropane hydrochloride (VIId)

16.1 ml (0.24 mol) of 3-chloropropanol was added dropwise into 13.4 ml (0.2 mol) of dimethylamine, and the mixture was heated to the reflux temperature and reacted for 4 h. After cooling to room temperature, 40 ml of 4N NaOH solution and 30 ml benzene were added into the reaction mixture. The mixture was stirred vigorously, and a benzene layer was separated out after standing. The aqueous layer was washed with benzene, and the combined benzene layers were dried over anhydrous sodium sulfate. The mixture was filtrated in a reduced pressure and the filtrate was concentrated to obtain 22 ml of product, as an oil. This oil was dissolved with 40 ml carbon tetrachloride and cooled by ice-water bath. Into the oil, 10 ml solution of thionyl chloride dissolved in 10 ml carbon tetrachloride was added dropwise. The mixture was reacted for 4 h at room temperature, and concentrated to dry in a reduced pressure. The residue was recrystallized with ethyl acetate and dried to obtain 17.5 g white acicular crystal with the yield of 60.8%. m.p. 140-142° C.

Example 15

Preparation of 2-diethylamino chloroethane hydrochloride (VIIe)

16.1 ml (0.24 mol) of chlorohydrin was added dropwise into 20.6 ml (0.2 mol) of dimethylamine, and the mixture was heated to the reflux temperature and reacted for 4 h. The reaction mixture was cooled to room temperature and 40 ml of 4 N NaOH solution and 30 ml of benzene were added into the mixture. The mixture was stirred vigorously and a benzene layer was separated out after standing. The aqueous layer was washed with benzene, and the combined benzene layers were dried over anhydrous sodium sulfate. The mixture was filtrated in a reduced pressure and the filtrate was concentrated to obtain 22 ml of product, as an oil. This oil was dissolved with 40 ml carbon tetrachloride and cooled by ice-water bath. Into the oil, 10 ml solution of thionyl chloride dissolved in 10 ml carbon tetrachloride was added dropwise. The mixture was reacted for 4 h at room temperature, and concentrated to dry in a reduced pressure. The residue was recrystallized with ethyl acetate and dried to obtain 16.1 g white acicular crystal with the yield of 46.6%. m.p. 207-210° C.

Example 16

Preparation of 3-diethylamino chloropropane hydrochloride (VIIf)

10 ml toluene, 3 ml (28.9 mmol) of diethylamine and 2.9 ml (34.6 mmol) of 3-chloropropanol were added successively into a reaction flask, and the mixture was heated to the reflux temperature and reacted for 6 h. After cooling to room temperature, the mixture was washed with 5% NaOH solution and saturated saline solution, successively, and dried over anhydrous sodium sulfate, then filtered. 4.2 ml (57.7 mmol) of thionyl chloride was added dropwise into the filtrate in an ice-bath, and the mixture was stirred at room temperature overnight. The reaction solution was concentrated to dry in a reduced pressure and the residue was recrystallized with absolute ethyl alcohol to obtain 2.1 g white solid with the yield of 40%. m.p. 80-82° C.

Example 17

Preparation of N-(2-chloroethyl)-4-methyl piperazine dihydrochloride (VIIg)

10 ml of 25% NaOH and 1 ml (9 mmol) of 4-methyl piperazine were added successively into a reaction flask. The mixture was heated up to 50° C., and 1.8 ml (18 mmol) 1-bromo-2-chloroethane was added dropwise. The mixture was reacted at 50° C. for 6 h, then cooled to room temperature. The reaction solution was extracted with ethyl acetate, and the extraction was washed with saturated saline solution and dried over anhydrous sodium sulfate, then filtered. The filtrate was concentrated to dry in a reduced pressure and a small amount of ethanol/NaOH solution was added dropwise into the residue. The mixture was shaken and placed in a refrigerator for standing, then concentrated to dry in a reduced pressure to obtain 0.43 g white solid with the yield of 23%. m.p. 227-230° C.

Example 18

Preparation of N-(3-chloropropyl)-4-methyl piperazine hydrochloride(VIIh)

10 ml of 25% NaOH and 1 ml (9 mmol) of 4-methyl piperazine were added successively into a reaction flask. The mixture was heated up to 50° C., and 1.8 ml (18 mmol) 1-bromo-3-chloropropane was added dropwise into the mixture. After reacting at 50° C. for 6 h, the reaction mixture was cooled to room temperature and extracted with ethyl acetate. The extraction was washed with saturated saline solution and dried over anhydrous sodium sulfate, then filtrated in a reduced pressure. The filtrate was concentrated to dry and a small amount of ethanol/NaOH solution was added dropwise into the residue. The mixture was shaken and placed in a refrigerator for standing, then concentrated to dry in a reduced pressure to obtain 0.21 g white solid with the yield of 11%. m.p. 255-257° C.

Example 19

Preparation of N-(2-chloroethyl)tetrahydropyrrole hydrochloride (VIIi)

165 ml (2 mol) of tetrahydropyrrole, 67 ml (1 mol) of 2-chlorohydrin and 200 ml toluene were added successively into a reaction flask. The mixture was heated to the reflux temperature and reacted for 3 h. After cooling to room temperature, a solid was separated out. The solid was filtered by sucking, and the filter cake was washed with 20 ml toluene. The temperature of the filtrate was controlled at about 75° C., and 200 ml thionyl chloride was added dropwise. After refluxing for 2 h, the mixture was cooled to room temperature and then concentrated to dry in a reduce pressure. The residue was recrystallized with absolute ethyl alcohol to obtain 105 g white solid with the yield of 62.3%. m.p. 198-203° C.

Example 20

Preparation of N-(2-chloroethyl)tetrahydropyrrole hydrochloride (VIIj)

165 ml (2 mol) of tetrahydropyrrole, 67 ml (1 mol) of 3-chloropropanol and 200 ml toluene were added successively into a reaction flask. The mixture was heated to the reflux temperature and reacted for 3 h. After cooling to room temperature, a solid was separated out. The solid was filtered by sucking, and the filter cake was washed with 20 ml toluene. The temperature of the filtrate was controlled at about 75° C., and 200 ml thionyl chloride was added dropwise. After refluxing for 2 h, the mixture was cooled to room temperature and then concentrated to dry in a reduce pressure. The residue was recrystallized with absolute ethyl alcohol to obtain 105 g white solid with the yield of 62.3%. m.p. 169-173° C.

Example 21

Preparation of 2-diisopropylamino chloroethane hydrochloride (VIIk)

3.6 ml (53.6 mmol) of 2-chlorohydrin was added dropwise into 5 ml (35.7 mmol) of diisopropylamine. The mixture was heated to the reflux temperature and reacted for 5 h. After cooling to room temperature, 8% KOH and 10 ml benzene were added. The mixture was stirred and the benzene layer separated was washed with a saturated saline solution, then dried over anhydrous sodium sulfate and filtrated. Into the filtrate, 5.2 ml (71.3 mmol) of thionyl chloride was added dropwise. The mixture was reacted for 12 h at room temperature, then concentrated to dry in a reduced pressure to obtain 2.73 g white solid with the yield of 38%. m.p. 129-131° C.

Example 22

Preparation of N-(2-chloroethyl) morpholine hydrochloride (VIII)

Into 5 g (57 mmol) morpholine dissolved in 15 ml toluene, 4.6 ml (69 mmol) of 2-chlorohydrin was added dropwise. The mixture was heated to the reflux temperature and reacted for 5 h. After cooling, 20 ml of 5% NaOH solution was added to wash the reaction mixture. The organic layer obtained was washed with a saturated saline solution and dried over anhydrous sodium sulfate, then filtrated. Into the filtrate cooled in an ice bath, 8.3 ml (114 mmol) of thionyl chloride was added dropwise. After reacting for 12 h at room temperature, the reaction mixture was concentrated to dry in reduced pressure. The residue was recrystallized with ethyl acetate to obtain 5.9 g white solid with the yield of 55%. m.p. 182-184° C.

Example 23

Preparation of N-(3-chloropropyl) morpholine hydrochloride (VIIm)

5 ml acetonitrile, 2.3 ml (23 mmol) of 1-bromo-3-chloropropane and 1 ml (11.5 mmol) of morpholine were added successively into a reaction flask. The mixture was stirred for 1 h, and 0.5 ml of 5% NaOH solution was added. After stirring at room temperature for 12 h, 3 ml concentrated hydrochloric acid and 10 ml water were added into the mixture. The lower layer was discarded, and the upper layer was alkalified with 5% NaOH and extracted with ethyl acetate. The organic layer was washed with a saturated saline solution and dried over anhydrous sodium sulfate, then filtered. The filtrate was concentrated to dry in a reduced pressure, and a small amount of ethanol/NaOH solution was added dropwise into the residue. The mixture was shaken and placed in a refrigerator for standing, then concentrated to dry in a reduced pressure to obtain 1.4 g white solid with the yield of 60%. m.p. 168-170° C.

Example 24

Preparation of 6-(4-(2-piperidinylethoxy)phenyl)-5H-indeno[1,2-c]isoquinoline-5,11(6H)-diketone (Ia)

0.3 g (0.88 mmol) of Compound VIa, 0.49 g (3.54 mmol) of potassium carbonate, 0.24 g (1.33 mmol) of Compound VIIa and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.12 g red solid with the yield of 30%. m.p. 98-102° C. $^1$H-NMR (CDCl$_3$): 5.66-8.74 (12H, m, Ar—H), 4.28 (2H, t, J=5.7 Hz, OCH$_2$), 2.91 (2H, t, J=5.7 Hz, NCH$_2$), 2.63 (4H, brs, 2,6-piperidyl), 1.69 (4H, brs, 3,5-piperidyl), 1.54 (2H, brs, 4-piperidyl). EI-MS m/z: 450 [M]$^+$.

Example 25

Preparation of 6-(4-(3-piperidinylpropoxy)phenyl)-5H-indeno[1,2-c]isoquinoline-5,11(6H)-diketone (Ib)

0.19 g (0.56 mmol) of Compound VIa, 0.3 g (2.24 mmol) of potassium carbonate, 0.17 g (0.84 mmol) of Compound VIIb and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.08 g red solid with the yield of 31%. m.p. 132-138° C. $^1$H-NMR (CDCl$_3$): 5.66-8.74 (12H, m, Ar—H), 4.20 (2H, t, J=6.3 Hz, OCH$_2$), 2.76 (6H, m, NCH₂), 2.70 (2H, brs, CH₂), 1.85 (4H, brs, 3,5-piperidyl), 1.59 (2H, brs, 4-piperidyl). EI-MS m/z: 464[M]⁺.

Example 26

Preparation of 6-(4-(2-dimethylaminoethoxy)phenyl)-5H-indeno[1,2-c]isoquinoline-5,11(6H)-diketone (Ic)

0.35 g (1.03 mmol) of Compound VIa, 0.57 g (4.13 mmol) of potassium carbonate, 0.22 g (1.55 mmol) Compound VIIc and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.11 g red solid with the yield of 26%. m.p. 152-156° C. ¹H-NMR (CDCl₃): 5.30-8.33 (12H, m, Ar—H), 4.24 (2H, t, J=5.4 Hz, OCH₂), 2.91 (2H, t, J=5.4 Hz, NCH₂), 2.47 (6H, s, N (CH₃)₂). EI-MS m/z: 410 [M]⁺.

Example 27

Preparation of 6-(4-(3-dimethylaminopropoxy)phenyl)-5H-indeno[1,2-c]isoquinoline-5,11(6H)-diketone (Id)

0.2 g (0.59 mmol) of Compound VIa, 0.33 g (2.36 mmol) of potassium carbonate, 0.14 g (0.88 mmol) of Compound VIId and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.070 g red solid with the yield of 29%. m.p. 148-153° C. ¹H-NMR (CDCl₃): 5.30-7.76 (12H, m, Ar—H), 4.15 (2H, t, J=6.3 Hz, OCH₂), 2.52 (2H, t, J=6.3 Hz, NCH₂), 2.30 (6H, s, N(CH₃)₂), 2.04 (2H, m, CH₂). EI-MS m/z: 424[M]⁺.

Example 28

Preparation of 6-(4-(2-diethylaminoethoxy)phenyl)-5H-indeno[1,2-c]isoquinoline-5,11(6H)-diketone (Ie)

0.3 g (0.88 mmol) of Compound VIa, 0.49 g (3.54 mmol) of potassium carbonate, 0.3 g (1.77 mmol) of Compound VIIe and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.13 g red solid with the yield of 34%. m.p. 127-132° C. ¹H-NMR (CDCl₃): 5.65-8.74 (12H, m, Ar—H), 4.26 (2H, t, J=5.7 Hz, OCH₂), 3.05 (2H, t, J=5.7 Hz, NCH₂), 2.80 (4H, m, J=7.2 Hz, N (CH₂CH₃)₂), 1.21 (6H, m, J=7.2 Hz, N (CH₂CH₃)₂). EI-MS m/z: 438[M]⁺.

Example 29

Preparation of 6-(4-(3-diethylaminopropoxy)phenyl)-5H-indeno[1,2-c]isoquinoline-5,11(6H)-diketone (If)

0.5 g (1.49 mmol) of Compound VIa, 0.8 g (5.9 mmol) of potassium carbonate, 0.42 g (2.24 mmol) of Compound VIIf and 30 ml acetone successively were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.092 g red solid with the yield of 14%. m.p. 122-124° C. ¹H-NMR (CDCl₃): 5.65-8.74 (12H, m, Ar—H), 4.18 (2H, t, OCH₂), 2.71-2.93 (6H, m, NCH₂), 2.17 (2H, m, CH₂), 1.24 (6H, t, N (CH₂CH₃)₂). EI-MS m/z: 452[M]⁺.

Example 30

Preparation of 6-(4-(2-(4-methylpiperazinyl)ethoxy)phenyl)-5H-indeno[1,2-c]isoquinoline-5,11(6H)-diketone (Ig)

0.29 g (0.72 mmol) of Compound VIa, 0.2 g (1.44 mmol) of potassium carbonate, 0.14 g (1.44 mmol) of Compound VIIg and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.09747 g red solid with the yield of 23%. m.p. 136-140° C. ¹H-NMR (CDCl₃): 5.65-8.74 (12H, m, Ar—H), 4.24 (2H, t, J=5.4 Hz, OCH₂), 2.94 (2H, t, J=5.4 Hz, NCH₂), 2.67-2.79 (8H, m, N (CH₂CH₂)₂N), 2.43 (3H, s, NCH₃). EI-MS m/z: 465[M]⁺.

Example 31

Preparation of 6-(4-(3-(4-methylpiperazinyl)propoxy)phenyl)-5H-indeno[1,2-c]isoquinoline-5,11 (6H)-diketone (Ih)

0.25 g (0.74 mmol) of Compound VIa, 0.4 g (2.95 mmol) of potassium carbonate, 0.24 g (1.1 mmol) of Compound VIIh and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.097 g red solid with the yield of 28%. m.p. 179-182° C. ¹H-NMR(CDCl₃): 5.66-8.69 (12H, m, Ar—H), 4.13 (2H, t, J=6.3 Hz, OCH₂), 2.52-2.62 (10H, m, N(CH₂)₂), 2.32 (3H, s, NCH₃), 2.06 (2H, m, CH₂). EI-MS m/z: 479[M]⁺.

Example 32

Preparation of 6-(4-(2-pyrrolidinylethoxy)phenyl)-5H-indeno[1,2-c]isoquinoline-5,11(6H)-diketone (Ii)

0.2 g (0.59 mmol) of Compound VIa, 0.33 g (2.36 mmol) of potassium carbonate, 0.15 g (0.88 mmol) of Compound VIIi and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.08 g red solid with the yield of 32%. m.p. 94-98° C. $^1$H-NMR(CDCl$_3$): 5.65-7.73 (12H, m, Ar—H), 4.29 (2H, t, J=5.7 Hz, OCH$_2$), 3.07 (2H, t, J=5.7 Hz, NCH$_2$), 2.80 (4H, brs, NCH$_2$), 1.90 (4H, brs, CH$_2$CH$_2$). EI-MS m/z: 436[M]$^+$.

Example 33

Preparation of 6-(4-(3-pyrrolidinylpropoxy)phenyl)-5H-indeno[1,2-c]isoquinoline-5,11(6H)-diketone (Ij)

0.2 g (0.59 mmol) of Compound VIa, 0.33 g (2.36 mmol) of potassium carbonate, 0.15 g (0.88 mmol) of Compound VIIj and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.08 g red solid with the yield of 32%. m.p. 80-85° C. $^1$H-NMR(CDCl$_3$): 5.66-8.73 (12H, m, Ar—H), 4.24 (2H, t, J=6.3 Hz, OCH$_2$), 2.78 (2H, t, J=6.3 Hz, NCH$_2$), 2.58 (4H, brs, NCH$_2$), 2.27 (2H, m, CH$_2$) 1.87 (4H, brs, CH$_2$CH$_2$). EI-MS m/z: 450[M]$^+$.

Example 34

Preparation of 6-(4-(2-diisopropylaminoethoxy)phenyl)-5H-indeno[1,2-c]isoquinoline-5,11(6H)-diketone (Ik)

0.1 g (0.29 mmol) of Compound VIa, 0.16 g (1.18 mmol) of potassium carbonate, 0.09 g (0.44 mmol) of Compound VIIk and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.062 g red solid with the yield of 45%. m.p. 117-120° C. $^1$H-NMR(CDCl$_3$): 5.67-7.79 (12H, m, Ar—H), 4.02 (2H, t, J=7.2 Hz, OCH$_2$), 3.08-3.13 (2H, m, J=6.3 Hz, N(CH(CH$_3$)$_2$)$_2$), 2.88 (2H, t, J=7.2 Hz, NCH$_2$), 1.07 (12H, d, N(CH(CH$_3$)$_2$)$_2$). EI-MS m/z: 466[M]$^+$.

Example 35

Preparation of 6-(4-(2-morpholinylethoxy)phenyl)-5H-indeno[1,2-c]isoquinoline-5,11(6H)-diketone (Il)

0.13 g (0.37 mmol) of Compound VIa, 0.2 g (1.49 mmol) of potassium carbonate, 0.1 g (0.56 mmol) of Compound VIII and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.12 g red solid with the yield of 68.5%. m.p. 184-190° C. $^1$H-NMR(CDCl$_3$): 5.66-8.74 (12H, m, Ar—H), 4.28 (2H, brs, OCH$_2$), 3.815 (4H, brs, OCH$_2$), 2.94 (2H, brs, NCH$_2$), 2.69 (4H, brs, NCH$_2$). EI-MS m/z: 452[M]$^+$.

Example 36

Preparation of 6-(4-(3-morpholinylpropoxy)phenyl)-5H-indeno[1,2-c]isoquinoline-5,11(6H)-diketone (Im)

0.2 g (0.59 mmol) of Compound VIa, 0.33 g (2.36 mmol) of potassium carbonate, 0.18 g (0.88 mmol) of Compound VIIm and 30 ml acetone were added successively into a reaction flask. The mixture was heated to the reflux temperature and reacted for 12 h, then filtrated while it is still hot. The filtrate was concentrated to dry in a reduced pressure. The residue was dissolved with 20 ml dichloromethane, and the substance undissolved was filtered off. The filtrate was concentrated to dry in a reduced pressure and the residue was purified by column chromatography to obtain 0.077 g red solid with the yield of 32%. m.p. 166-172° C. $^1$H-NMR(CDCl$_3$): 5.68-8.39 (12H, m, Ar—H), 4.18 (2H, t, J=6.3 Hz, OCH$_2$), 3.78 (4H, brs, OCH$_2$), 2.43-2.61 (6H, m, NCH$_2$), 2.00 (2H, brs, CH$_2$). EI-MS m/z: 466[M]$^+$.

Example 37

Preparation of 6-(4-(2-dimethylaminoethoxy)phenyl)-3-methoxyl-5H-indeno[1,2-c]isoquinoline-5,11(6H)-diketone (In)

0.3 g (0.81 mmol) of Compound VIb, 0.45 g (3.25 mmol) of potassium carbonate, 0.35 g (2.44 mmol) of Compound VIIk and 10 ml acetone were added successively into a reaction flask. The mixture was heated to the reflux temperature and reacted for 12 h, then filtrated while it is still hot. The filtrate was concentrated to dry in a reduced pressure. The residue was dissolved with 15 ml dichloromethane, and the substance undissolved was filtered off. The filtrate was concentrated to dry in a reduced pressure and the residue was purified by column chromatography to obtain 0.245 g red solid with the yield of 68.5%. m.p. 116-119° C. $^1$H-NMR (CDCl$_3$): 5.60-7.73 (11H, m, Ar—H), 4.20 (2H, t, J=5.4 Hz, OCH$_2$), 2.87 (2H, t, J=5.4 Hz, NCH$_2$), 2.47 (6H, s, N(CH$_3$)$_2$). EI-MS m/z: 440[M]$^+$.

Embodiment 38

Preparation of 6-(4-(2-dimethylaminoethoxy)phenyl)-3-hydroxy-5H-indeno[1,2-c]isoquinoline-5,11(6H)-diketone (Io)

0.1 g (0.23 mmol) of Compound In was dissolved in 5 ml of 48% hydrobromic acid solution, and the mixture was heated to the reflux temperature and reacted for 48 h. After cooling to room temperature, a saturated sodium carbonate solution was added to adjust the pH value to be neutral. The reaction mixture was extracted with 20 ml dichloromethane, and the extraction was dried over anhydrous sodium sulfate and filtrated. The filtrate was concentrated to dry in a reduced pressure, and the residue was purified via column chromatography to obtain 0.029 g red solid with the yield of 30%. m.p. 145-149° C. $^1$H-NMR(CDCl$_3$): 9.50 (1H, s, OH), 5.32-8.35 (11H, m, Ar—H), 4.21 (2H, t, J=5.4 Hz, OCH$_2$), 2.90 (2H, t, J=5.4 Hz, NCH$_2$), 2.48 (6H, s, N(CH$_3$)$_2$). EI-MS m/z: 426 [M]$^+$.

Embodiment 39

Preparation of 6-(4-(2-dimethylaminoethoxy)phenyl)-3,9-dimethoxy-5H-indeno[1,2-c]isoquinoline-5,11(6H)-diketone (Ip)

0.3 g (0.75 mmol) of Compound VIc, 0.26 g (1.88 mmol) of potassium carbonate, 0.32 g (2.26 mmol) of Compound VIIk and 10 ml acetone were added successively into a reaction flask. The mixture was heated to the reflux temperature and reacted for 12 h, then filtrated while it is still hot. The filtrate was concentrated to dry in a reduced pressure. The residue was dissolved with 15 ml dichloromethane, and the substance undissolved was filtered off. The filtrate was concentrated to dry in a reduced pressure and the residue was purified by column chromatography to obtain 0.19 g red solid with the yield of 54%. m.p. 120-124° C. $^1$H-NMR(CDCl$_3$): 5.62-7.76 (10H, m, Ar—H), 4.19 (2H, t, J=5.4 Hz, OCH$_2$), 2.83 (2H, t, J=5.4 Hz, NCH$_2$), 2.45 (6H, s, N(CH$_3$)$_2$). EI-MS m/z: 470 [M]$^+$.

Embodiment 40

Preparation of 6-(4-(2-dimethylaminoethoxy)phenyl)-3,9-dihydroxy-5H-indeno[1,2-c]isoquinoline-5,11(6H)-diketone (Iq)

0.1 g (0.21 mmol) of Compound Ip was dissolved in 5 ml of 48% hydrobromic acid, and the solution was heated to the reflux temperature and reacted for 48 h. After cooling to room temperature, a saturated sodium carbonate solution was added to adjust the pH value to be neutral. The reaction mixture was extracted with 20 ml dichloromethane, and the extraction was dried over anhydrous sodium sulfate and filtrated. The filtrate was concentrated to dry in a reduced pressure, and the residue was purified via column chromatography to obtain 0.025 g red solid with the yield of 27%. m.p. 141-143° C. $^1$H-NMR(CDCl$_3$):9.48 (1H, s, OH), 5.30-8.31 (10H, m, Ar—H), 4.23 (2H, t, J=5.4 Hz, OCH$_2$), 2.92 (2H, t, J=5.4 Hz, NCH$_2$), 2.47 (6H, s, N(CH$_3$)$_2$). EI-MS m/z: 442 [M]$^+$.

Embodiment 41

0.5 g compound prepared in Example 30, 2 g starch and 1 g dextrin were mixed with an appropriate amount of 30% ethanol as a wetting agent, then granulated and tablettized.

What is claimed is:

1. A compound of formula 1 or the pharmaceutically acceptable salts thereof:

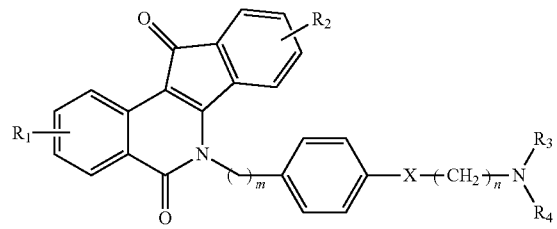

Wherein $R_1$ and $R_2$ independently represent H, OH, $C_1$-$C_4$ alkoxy or $C_1$-$C_6$ alkoxycarbonyl;

$R_3$ and $R_4$ independently represent —CO(CH$_2$)$_2$CH$_3$, —CO(CH$_2$)$_3$CH$_3$ or $C_1$-$C_6$ alkyl; or $R_3$ and $R_4$, when combined with their adjacent nitrogen atom, represent piperidyl, 2-methylpiperidyl, homopiperidyl, morpholinyl, pyrrolidinyl, 3-methylpyrrolidinyl, 3,3-dimethylpyrrolidinyl, 3,4-dimethoxypyrrolidinyl, piperazinyl, N-methylpiperazinyl, N-ethylpiperazinyl, N-phenylpiperazinyl or N-benzylpiperazinyl;

X represents O, S, NH, CH$_2$ or —CO—;

m=0 or 1; and n=2 or 3.

2. The compounds or the pharmaceutically acceptable salts thereof according to claim 1, wherein X represents O or S.

3. The compounds or the pharmaceutically acceptable salts thereof according to claim 1, wherein $R_1$ and $R_2$ independently represent OH or methoxyl.

4. A process for preparing the compound according to claim 1, comprising:

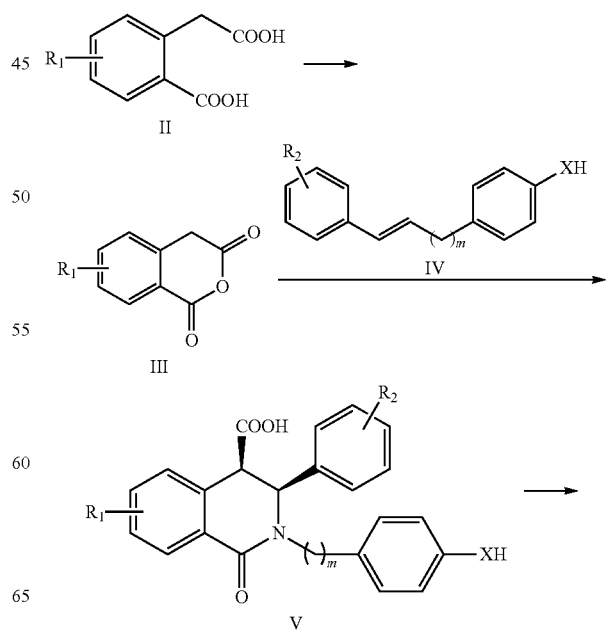

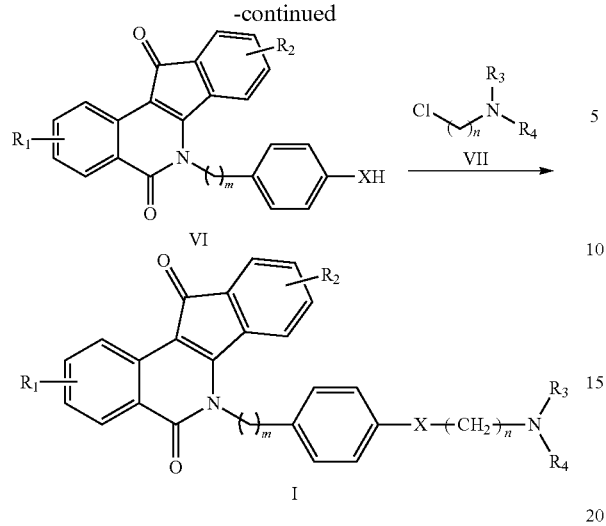
Wherein $R_1$, $R_2$, $R_3$, $R_4$, X, m and n are defined same as in claim 1.
5. A pharmaceutical composition, containing the compound or the pharmaceutically acceptable salt thereof according to claim 1 and a pharmaceutically acceptable carrier.
* * * * *